United States Patent
Berwaer et al.

(10) Patent No.: US 6,262,057 B1
(45) Date of Patent: Jul. 17, 2001

(54) PSEUDOPOLYMORPHIC FORMS OF 2-[2-[4-[BIS(4-FLUOROPHENYL)METHYL]-1-PIPERAZINYL]ETHOXY]ACETIC ACID DIHYDROCHLORIDE

(75) Inventors: Monique Berwaer, Ham-sur-Heure; Guy Bodson, Bellefontaine; Michel Deleers, Linkebeek; Charles Dogimont, Brussels; Domenico Fanara, Wanze; Jacques Timmermans, Virginal, all of (BE)

(73) Assignee: UCB, S.A., Brussels (BE)

( * ) Notice: Subject to any disclaimer, the term of this patent is extended or adjusted under 35 U.S.C. 154(b) by 0 days.

(21) Appl. No.: 09/555,021
(22) PCT Filed: Nov. 26, 1998
(86) PCT No.: PCT/BE98/00184
  § 371 Date: May 23, 2000
  § 102(e) Date: May 23, 2000
(87) PCT Pub. No.: WO99/28310
  PCT Pub. Date: Jun. 10, 1999

(30) Foreign Application Priority Data

Nov. 26, 1997 (EP) .................................................. 97870193

(51) Int. Cl.⁷ ..................... A61K 31/495; C07D 295/14; C07D 295/145
(52) U.S. Cl. ...................... 514/255.04; 544/396
(58) Field of Search ........................ 544/396; 514/255.04

(56) References Cited

U.S. PATENT DOCUMENTS

| 4,525,358 | 6/1985 | Baltes et al. ........................ 514/255 |
| 5,419,898 | * 5/1995 | Ikejiri et al. ...................... 424/78.04 |
| 5,968,551 | * 10/1999 | Oshlack et al. ..................... 424/456 |

FOREIGN PATENT DOCUMENTS

| 0 058 146 | 8/1982 | (EP) . |
| 0 801 064 | 10/1997 | (EP) . |
| 2 351 964 | 12/1977 | (FR) . |
| 1 174 819 | 12/1969 | (GB) . |
| 1 561 286 | 2/1980 | (GB) . |
| 2 225 320 | 5/1990 | (GB) . |
| 2 225 321 | 5/1990 | (GB) . |
| 135643 | 4/1997 | (PK) . |
| 97/37982 | 10/1997 | (WO) . |
| 97/2973 | 1/1998 | (ZA) . |

* cited by examiner

*Primary Examiner*—Emily Bernhardt
(74) *Attorney, Agent, or Firm*—Wenderoth, Lind & Ponack, LLP

(57) ABSTRACT

The present invention relates to new pseudopolymorphic forms of 2-[2-[4-[bis(4-fluorophenyl)methyl]-1-piperazinyl] ethoxy]acetic acid dihydrochloride, namely, anhydrous 2-[2-[4-[bis(4-fluorophenyl)methyl]-1-piperazinyl]ethoxy]acetic acid dihydrochloride and 2-[2-[-bis(4-fluorophenyl)methyl]-1-piperazinyl]ethoxy]acetic acid dihydrochloride monohydrate. It also relates to processes for the preparation of these pseudopolymorphic forms and to pharmaceutical compositions containing them.

6 Claims, No Drawings

PSEUDOPOLYMORPHIC FORMS OF 2-[2-[4-[BIS(4-FLUOROPHENYL)METHYL]-1-PIPERAZINYL]ETHOXY]ACETIC ACID DIHYDROCHLORIDE

The present invention relates to new pseudopolymorphic crystalline forms of 2-[2-[4-[bis(4-fluorophenyl)methyl]-1-piperazinyl]ethoxy]acetic acid dihydrochloride, to processes for their preparation and to pharmaceutical compositions containing them.

2-[2-[4-[Bis(4-fluorophenyl)methyl]-1-piperazinyl]ethoxy]acetic acid, also known and hereinafter referred to as efletirizine (INN: International Non-proprietary Name), is the compound of the following formula:

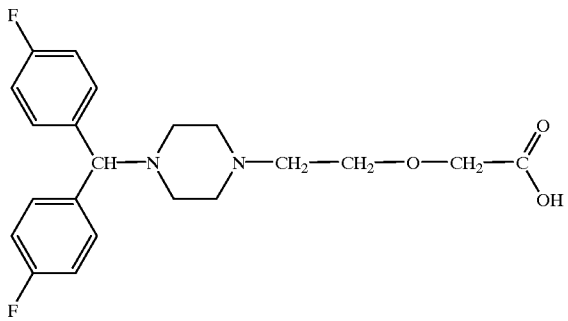

Efletirizine is encompassed within general formula I of European patent No. 58146 in the name of the applicant, which relates to substituted benzhydrylpiperazine derivatives.

Like 2-[2-[4-1(4-chlorophenyl)phenylmethyl]-1-piperazinyl]ethoxy]acetic acid, also known and hereinafter referred to as cetirizine (INN), efletirizine has been found to possess excellent antihistaminic properties. It belongs to the pharmacological class of second generation histamine $H_1$-receptor antagonists and shows in vitro high affinity and selectivity for $H_1$-receptors. Like cetirizine, it is useful as an antiallergic, antihistaminic, bronchodilator and antispasmodic agent. Recent clinical studies have shown the utility of efletirizine when administered in the form of a nasal spray for the treatment of allergic rhinitis and rhino-conjunctivitis (J. -F. Dessanges et al., Allergy and Clin. Immunol. News (1994), Suppl. n°2, abstract 1864; C. De Vos et al., Allergy and Clin. Immunol. News (1994), Suppl. n°2, abstract 428).

Another recent clinical pharmacology study (to be published) has shown that efletirizine gives unexpectedly good results In the treatment of urticaria, atopic dermatitis and prurit.

Due to increasing therapeutic interest for efletirizine, we have set out to prepare pharmaceutical compositions containing efletirizine.

Efletirizine is an amorphous solid. However, it is highly desirable to dispose of a product with reproducible characteristics, which always performs in the same way during formulation. in particular in order to comply with regulatory requirements. For these reasons, we attempted to prepare crystalline forms of efletirizine. Although efletirizine has been studied for its therapeutic utility, no attention has yet been given to such crystalline forms.

The present invention derives from the unexpected discovery of two pseudopolymorphic crystalline forms of efletirizine dihydrochloride, namely anhydrous efletirizine dihydrochloride and efletirizine dihydrochloride monohydrate. For the sake of identification, anhydrous efletirizine dihydrochloride will be hereinafter designated as "Form A" and efletinzine dihydrochloride monohydrate will be hereinafter designated as "Form B".

According to another embodiment, the present invention provides processes for the preparation of these new pseudopolymorphic forms, and further provides processes for the conversion of Form A into Form B and of Form B into Form A.

The present invention also derives from the discovery that these two new pseudopolymorphic forms have different properties. In particular, we have discovered that solid pharmaceutical compositions comprising Form A of efetirizine dihydrochloride exhibit better storage stability over time than solid pharmaceutical compositions comprising Form B. This better storage stability appears to be due to better compatibility with the solid carriers and diluents commonly used in such solid pharmaceutical compositions.

Accordingly, the present invention also relates to pharmaceutical compositions comprising Form A or Form B in association with suitable pharmaceutical excipients, carriers or diluents therefor. preferably to solid pharmaceutical compositions comprising Form A.

As to the preparation processes of these pseudopolyinorphic forms of efletirizine dihydrochloride. Form B may be obtained by hydrolysis in an aqueous medium of 2-[4-[bis(4-fluorophenyl)methyl]-1-piperazinyl]ethoxyacetamide in the presence of hydrochloric acid, at a temperature comprised between 40° C. and the reflux temperature of the reaction mixture. Form B can then be recrystallised in aqueous acid or in a mixture of solvents containing water and hydrochloric acid.

Form B can then be transformed into Form A by heating up'to reflux in a solvent, such as acetone or methylethylketone. Optionally, Form A can be converted back into Form B by recrystallisation in aqueous hydrochloric acid.

The following examples illustrate processes for the preparation of efletirizine dihydrochloride Form A and Form B according to the present invention. In these examples, differential thermograms were recorded on a PERKIN ELMER Differential Scanning Calorimeter DSC 7 with a temperature gradient of 20° C./min.

1. Preparation of 2-[4-[bis(4-fluorophenyl)methyl]-1-piperazinyl]ethoxyacetamide and of 2-[4-[bis(4-fluorophenyl)methyl]-1-piperazinyl]ethoxyacetamide Dihydrochloride.

A suspension of 11.0 g (0.038 mol) of 1-[bis-(4-fluorophenyl)methyl]piperazine, 10.5 g (0.076 mol) of 2-(2-chlorethoxy)acetamide and 8.1 g of anhydrous sodium carbonate In 40 ml of xylene is heated under reflux at 140° C. for 4 hours. The precipitate which forms is filtered off and then washed with toluene. The filtrate and toluene used for washing are combined. The resulting organic phase is extracted with 80 ml of IN aqueous hydrochloric acid, and the aqueous phase is washed twice with toluene. Toluene is added to the resulting aqueous phase, then 80 ml of a 1N aqueous sodium hydroxyde solution are added, and the aqueous mixture is extracted once with toluene. The organic phase is washed once with water, dried over anhydrous sodium sulphate and the solvents are evaporated off with a rotative evaporator until dryness. At this stage, the evaporation residue consists of 2-[4-[bis(4-fluorophenyl)methyl]-1-piperazinyl]ethoxyacetamide, which may be converted into its dihydrochloride salt as follows: the evaporation residue is taken up with 50 ml isopropanol and filtered; a 4.38 N alcoholic hydrochloric acid solution (17.5 ml) is added to the isopropanol solution and the mixture is allowed to crystallize. The precipitate is filtered, washed with isopropanol and diethyl ether, then dried in vacuo. This way, 15.8 g (90%) 2-[4-[bis(4-fluorophenyl)methyl]-1-piperazinyl]ethoxyacetamide dihydrochloride are obtained.

| Melting point: | 229.51° C. |
|---|---|
| Mass spectrum: | 389 (free base M$^+$). 345 and 203 |

2. Preparation of Efletirizine.

In a round-bottomed flask fitted with a mechanical stirrer, a Nitrogen inlet and a condenser, 30 g (0.065 mole) of 2-[4-[bis(4-fluorophenyl)methyl]-1-piperazinyl]ethoxyacetamide dihydrochloride are added to a mixture of 325 ml of ethanol, 130 ml of a 1 N aqueous sodium hydroxyde solution and 62 ml of a 6.3 N aqueous sodium hydroxide solution. The mixture is heated under reflux and under a Nitrogen atmosphere for 1.5 hours. The reaction mixture is then cooled down to room temperature and its pH is adjusted to 5 with 78 ml of a 5 N aqueous hydrochloric acid solution. Water is added, and ethanol is evaporated off under vacuum using a rotary evaporator. The resulting aqueous phase is extracted with dichloromethane. The organic phase is dried over anhydrous sodium sulphate and evaporated to dryness to give 25 g of crude efletirizine as an amorphous solid, 5 g of which are recrystallized in acetonitrile.

| Analysis for $C_{21}H_{24}F_2N_2O_3$: | | | | |
|---|---|---|---|---|
| calc. | C: 64.60 | H: 6.19 | N: 7.17 | F: 9.73 |
| found | C: 64.45 | H: 6.27 | N: 7.24 | F: 9.44 |

3. Preparation of Efletirizine Dihydrochloride Monohydrate (Form B).

A 37% (w/w) aqueous hydrochloric acid solution (6.38 l) is added to a suspension of 2.76 kg (7.1 mole) 2-[4-[bis(4-fluorophenyl)methyl]-1-piperazinyl]ethoxyacetamide in 6.4 l of water. The reaction mixture is heated at 65° C. for 1 hour. It is then cooled down to about 0° C. and allowed to crystallize. The precipitate which forms is filtered off at 0C, washed with HCl 6N (1.5 l), and crude efletirizine dihydrochloride monohydrate is obtained.

The crude product is then dissolved by heating at 60° C. in 13.5 l of water, and the solution is washed twice with 1 l toluene. The aqueous phase is then acidified with 16 l of a 37% (w/w) aqueous hydrochloric acid solution and cooled to 0° C. The precipitate which forms is filtered off at 0° C. washed with HCl 6N (2.4 l), and the product is dried at about 50° C. for 4 days. Efletirizine dihydrochloride monohydrate is obtained as a white solid (yield: 3.14 kg: 92%).

The differential scanning thermogram of Form B shows a first endotherm peak between 155 and 170° C. and a second endotherm peak between 210 and 235° C.

4. Preparation of Anhydrous Efletirizine Dihydrochloride (Form A), Conversion of Form B into Form A.

A suspension of 3.143 kg (6.53 mol) of Form B prepared at example 3 in 35 l methylethylketone is prepared. The mixture is heated up to reflux temperature for 2 hours. Water is removed at reflux temperature during 2 hours and 50 minutes while adding progressively 5 l of methylethylketone. The resulting mixture is cooled to 25° C., stirred for one night, then filtered and washed with methylethylketone (10 l). This way, anhydrous efletirizine dthydrochloride (Form A) is obtained, which is dried at 50° C. under vacuum (Yield: 98.6%. 2983 g).

| Analysis for $C_{21}H_{24}F_2N_2O_3.2HCl$: | | | | |
|---|---|---|---|---|
| calc. | C: 54.44 | H: 5.66 | N: 6.05 | Cl: 15.30 | F: 8.19 |
| found | C: 54.80 | H: 5.68 | N: 5.86 | Cl: 15.50 | F: 8.21 |

The differential scanning thermogram of Form A shows an endotherm peak between 220 and 235° C.

5. Conversion of Form A into Form B.

A suspension of 699 g of Form A prepared at example 4 in 3 l water is prepared. The mixture is heated at 60° C. until complete dissolution and is immediately filtered. A 37% (w/w) aqueous hydrochloric acid solution (3 l) is added at 50° C. to this solution over a period of 30 min. Crystallisation is then initiated with a few crystals of Form B. The mixture is cooled. stirred for 1 hour at room temperature, then for 2 hours at 0° C. The solid which forms is filtered off, washed with 0.6 l of a 6N aqueous hydrochloric acid solution and dried under vacuum at 50° C. (yield: 676 g: 93%).

| Analysis for $C_{21}H_{25}F_2N_2O_3.2HCl.H_2O$: | | | | |
|---|---|---|---|---|
| calc. | C: 52.41 | H: 5.86 | N: 5.82 | Cl: 14.73 | F: 7.89 |
| found | C: 52.08 | H: 6.03 | N: 5.44 | Cl: 14.55 | F: 7.83 |

Pseudopolymorphic efletirizine dihydrochloride Forms A and B have been further characterised by their respective X-ray powder diffraction spectra and intrinsic dissolution rates.

I. X-ray Powder Diffraction Spectra.

X-ray powder diffraction spectra were recorded on a PHILIPS PW 1710 diffractometer using the CuK$_\alpha$ radiation as source. The samples of powder to be analyzed were poured into the sample holder without grinding or mixing. The spectra were recorded at room temperature from 2θ=4° to 2θ=50° with a scan speed of 1°/min.

For Form A, characteristic diffraction peaks are observed at 2θ values of: 13.7°±0.5; 13.9°±0.5; 16.3°±0.5; 18.0°±0.5; 18.6°±0.5; 19.1°±0.5; 23.1°±0.5; 24.1°±0.5; 25.6°±0.5; and 30.2°±0.5.

For Form B. characteristic diffraction peaks are observed at 2θ values of: 7.5°±0.5; 9.7°±0.5; 10.5°±0.5; 10.7°±0.5; 15.7°±0.5; 18.9°±0.5; 19.6°±0.5; 19.9°±0.5; 20.4°±0.5; 20.9°±0.5; 22.2°±0.5; 22.5°±0.5; 24.6°+0.5; 24.7°±0.5; 25.9°±0.5; and 29.3°±0.5.

II. Intrinsic Dissolution Rate.

Drug bioavailability studies have shown that an intrinsic dissolution rate (IDR) lower than 0.1 mg/cm$^2$/min can often be predictive of a dissolution rate-limited absorption in humans. Thus, IDR is a predictive parameter of bioavailability. This parameter depends upon various physicochemical properties including, the chemical form (salt, solvate), the crystal form, the solubility and wettability.

The determination of IDR was performed in the following way. The Form to be tested was homogeneously ground and mixed with microcrystalline cellulose AVICEL PH102 (dry binder which improves tableting properties). The substance:excipient mix ratio was 70:30 (w/w). Aliquots (500 mg) were compressed into pellets by compression until a final applied load of 10 tons In order to obtain a constant and known surface area of zero porosity.

The dissolution experiments were carried out at 37° C. using 500 ml of aqueous media at three different pH values intended to cover the expected range of human gastrointestinal pH values, i.e. 1.2. 4.0 and 7.5. Uniform and reproducible haemodynamic conditions were obtained by carrying out the test with USP XII apparatus N°2 (United States Pharmacopoeia, 1990) in which a paddle is used as stirring element (50 rpm) and the pellet assembly is placed at the bottom of the vessel (static disc method). Statistically assessed (p<0.05) linear portions of all replicate dissolution curves were selected for subsequent IDR calculation.

The results are presented in Table 1 which shows the IDRs of Form A and Form B expressed in mg/cm$^2$/min at the three pHs tested.

TABLE 1

Intrinsic dissolution rates.

Intrinsic dissolution rate (mg/cm$^2$/min)

| pH | Form A | Form B |
|---|---|---|
| 1.2 | 5.04 ± 0.34 | 4.05 ± 0.64 |
| 4.0 | 5.43 ± 0.32 | 3.58 ± 0.50 |
| 7.5 | 4.52 ± 0.34 | 3.31 ± 0.04 |

The results of Table 1 show that both Form A and Form B have IDRs higher than 0.1 mg/cm$^2$/min at the three pHs tested. This indicates that dissolution is probably not the rate-limiting step in the in vivo absorption process for solid pharmaceutical compositions containing either Form A or Form B. However, Form B has significantly lower IDRs than Form A. This means that if the fastest possible dissolution of a solid dosage form is wanted from a therapeutic point of view, Form A is the preferred crystalline form for use in a solid pharmaceutical composition.

The present invention also concerns pharmaceutical compositions comprising Form A or Form B in association with suitable pharmaceutical excipients therefor. In the case of solid pharmaceutical compositions, it is surprisingly more advantageous to use Form A rather than Form B. We have indeed discovered that solid pharmaceutical compositions comprising Form A in association with the usual carriers and diluents therefor, such as sorbitol, exhibit better storage stability than those comprising Form B.

This is illustrated in the results of the following study, aimed at examining the stabilities of the two pseudopolymorphic forms in the presence of D-sorbitol during storage under stress temperature conditions, that is, in sealed vials at 40 or 60° C.

In this study, HPLC analysis of several samples was performed: Form A, Form B. D-sorbitol and 1:1 (w/w) mixtures of Form A or Form B with D-sorbitol.

Each sample was homogeneously ground and mixed. Aliquots (500 mg) were compressed into 13 mm diameter pellets at an applied load of 1 ton which a usual compression strength for pharmaceutical tablets. Each compact pellet was Immediately ground into a fine powder, and an aliquot was stored In a tightly sealed glass vial at 40 or 60° C. Samples were analysed by HPLC after 0, 4. 16 and 24 weeks. 7

In a first series of analyses. HPLC/UV spectra were collected using a Kontron HPLC system type 300 fitted with a UV detector. The column used was Supercosil RP_ABZ 250×4.6 mm I.D. 5 µm particle size, and the mobile phase used consisted of an acetonitrile/water 25:75 (v/v) mixture, the water containing 770 mg/l ammonium acetate. Samples to be analysed were dissolved in acetonitrile/water 25:75 (v/v) at a concentration of 2 mg/ml, and 10 µl of these solutions were injected in the HPLC system.

Upon comparing the HPLC spectra obtained for the individual components and for the binary mixtures, new peaks detected were considered Indicative of an interaction with D-sorbitol. When present, these new peaks were quantified and further identified by HPLC/MS analysis, using a VG Quattro spectrometer coupled onto a Kontron HPLC system.

By HPLC/UV. no modifications of the spectrograms were observed for pure Form A and Form B after storage at 400 or 60° C. for 4, 16 or 24 weeks. Pure D-sorbitol was not detected in HPLC/UV. For the binary mixtures, new peaks appeared in the spectrograms upon comparison with the spectra of pure Form A or Form B. The new peaks were particularly significant for Form B which had been stored at 60° C.

In HPLC/MS, the new peaks observed for the binary mixtures were identified as a sorbitol-efletirizine monoester and dehydrated forms of a sorbitol-efletirizine monoester. The latter appeared after longer storage periods than the former.

Table 2 shows the results of quantitative determination of sorbitol-efletirizine monoester formed in the binary mixtures upon storage at 400 or 60° C. Relative quantification of monoester was performed by HPLC-UV analysis.

TABLE 2

Quantification of sorbitol-efletirizine monoester over time.

| | Relative % area | | | |
|---|---|---|---|---|
| | 40° C. | | 60° C. | |
| Time (weeks) | Form A | Form B | Form A | Form B |
| 0 | 0 | 0 | 0.03 | 0.04 |
| 4 | 0.04 | 0.13 | 0.29 | 0.87 |
| 16 | 0.07 | 0.16 | 0.45 | 2.69 |
| 24 | 0.13 | 0.23 | 0.46 | 2.95 |

Table 2 shows that when Form A or Form B is compressed in a pellet with D-sorbitol and stored at 40° or 60° C., a sorbitol-efletirizine monoester forms in an amount which increases over time. Furthermore it shows that monoester formation Is quite low for Form A upon storage at 40° C. and 60° C. and for Form B upon storage at 40° C. However monoester formation is very significant for Form B upon storage at 60° C.

These results show that Form A of efletirizine dihydrochloride interacts less with hydroxylated excipients, carriers or diluents commonly used in solid pharamceutical compositions and that it is thus more suitable than Form B for the preparation of such compositions.

The present invention further relates to a pharmaceutical composition comprising Form A or Form B or a mixture of Form A and Form B in association with suitable excipients, diluents or carriers thereof. Pharmaceutical compositions of the invention may have various forms. Sustained release formulations are of particular interest, and even prefered compositions comprise a slow release excipient in combination With a cyclodextrine.

An example of a such composition is as follows: 30 mg anhydrous 2-[2-[4-[bis(4-fluorophenyl)methyl]-1-piperazinyl]ethoxy]acetic acid dihydrochloride; 14.7 mg Encompress®; 82.3 mg cyclodextrine; 70 mg Methocel® K15MCR; 1 mg Aerosil® 200: 2 mg magnesium stearate.

What is claimed is:

1. 2-[2-[4-[Bis(4-fluorophenyl)methyl]-1-piperazinyl] ethoxy]acetic acid dihydrochloride monohydrate wherein its X-ray diffraction pattern presents peaks at 2θ values of: 7.5°±0.5; 9.7°±0.5; 10.5°±0.5: 10.7°±0.5; 15.7°±0.5; 18.9°±0.5; 19.6°±0.5; 19.9°±0.5: 20.4°±0.5: 20.9°±0.5; 22.2°±0.5; 22.5°±0.5: 24.6°±0.5; 24.7°±0.5; 25.9°±0.5; and 29.3°±0.5.

2. Process for the preparation of 2-[2-[4-[bis(4-fluorophenyl)methyl]-1-piperazinyl]ethoxy]acetic acid dihydrochloride monohydrate according to claim 1, wherein 2-[4-[bis(4-fluorophenyl)methyl]-1-piperazinyl] ethoxyacetamide is hydrolysed in the presence of hydrochloric acid.

3. Process according to claim 2, wherein hydrolysis is conducted at a temperature comprised between 40° C. and the reflux temperature of the reaction mixture.

4. Process for the preparation of 2-[2-[4-[bis(4-fluorophenyl)methyl]-1-piperazinyl]ethoxy]acetic acid dihydrochloride monohydrate according to claim 1, wherein anhydrous 2-[2-[4-[bis(4-fluorophenyl)methyl]-1-piperazinyl]ethoxy]acetic acid dihydrochloride is recrystallised in aqueous hydrochloric acid.

5. Pharmaceutical composition comprising of 2-[2-[4-[bis(4-fluorophenyl)methyl]-1-piperazinyl]ethoxy]acetic acid dihydrochloride monohydrate according to claim 1 in association with suitable excipients, diluents or carriers thereof.

6. Pharmaceutical composition comprising a mixture of anhydrous 2-[2-[4-[bis(4-fluorophenyl)methyl]-1-piperazinyl]ethoxy]acetic acid dihydrochloride the X-ray diffraction pattern of which presents peaks at 2θ values of: 13.7°±0.5; 13.9°±0.5; 16.3°±0.5; 18.0°±+0.5; 18.6°±0.5; 19.1°±0.5; 23.1°±0.5; 24.1°±0.5; 25.6°±0.5; and 30.2°±0.5 and of 2-[2-[4-[bis(4-fluorophenyl)methyl]-1-piperazinyl] ethoxy]acetic acid dihydrochloride monohydrate the X-ray diffraction pattern of which presents peaks at 2θ values of: 7.5°±0.5; 9.7°±0.5; 10.5°±0.5; 10.7°±0.5; 15.7°±0.5; 18.9°±0.5; 19.6°±0.5; 19.9°+0.5; 20.4°±0.5; 20.9°±0.5; 22.2°±0.5; 22.5°±0.5; 24.6°±0.5; 24.7°±0.5; 25.9°±0.5; and 29.3°±0.5, in association with suitable excipients, diluents or carriers thereof.

* * * * *

UNITED STATES PATENT AND TRADEMARK OFFICE
CERTIFICATE OF CORRECTION

PATENT NO. : 6,262,057 B1
DATED : July 17, 2001
INVENTOR(S) : Monique Berwaer et al.

It is certified that error appears in the above-identified patent and that said Letters Patent is hereby corrected as shown below:

Column 1,
Line 55, change "dispose of" to -- have at one's disposal --;
Line 57, change "." after "formulation" to -- , --.

Column 2,
Line 11, change "efeti-" to -- efleti- --;
Line 22, change "pseudopolyinor-" to -- pseudopolymor- --.

Column 3,
Line 65, change "dthydrochloride" to -- dihydrochloride --.

Column 6,
Line 39, change "Is" to -- is --;
Line 44, change "exciplents" to -- excipients --;
Line 45, change "pharamceutical" to -- pharmaceutical --;
Line 55, change "With" to -- with --.

Signed and Sealed this

Twenty-sixth Day of February, 2002

Attest:

JAMES E. ROGAN
*Attesting Officer*    *Director of the United States Patent and Trademark Office*